(12) United States Patent
Landon (10) Patent No.: US 6,193,969 B1
(45) Date of Patent: Feb. 27, 2001

(54) ANTIBODY FRAGMENTS IN THERAPY

(75) Inventor: John Landon, London (GB)

(73) Assignee: Protherics Inc., Nashville, TN (US)

( * ) Notice: Subject to any disclaimer, the term of this patent is extended or adjusted under 35 U.S.C. 154(b) by 0 days.

(21) Appl. No.: 08/256,155

(22) PCT Filed: Jun. 3, 1994

(86) PCT No.: PCT/GB94/01209

§ 371 Date: Mar. 10, 1995

§ 102(e) Date: Mar. 10, 1995

(87) PCT Pub. No.: WO94/29347

PCT Pub. Date: Dec. 22, 1994

(30) Foreign Application Priority Data

Jun. 3, 1993 (GB) .................................................. 9311507
Feb. 10, 1994 (GB) .................................................. 9402593

(51) Int. Cl.$^7$ ................................................ A61K 39/395
(52) U.S. Cl. .................................. 424/158.1; 424/130.1; 424/133.1; 424/156.1; 424/145.1; 530/387.1; 530/388.24; 530/388.85; 530/389.1; 530/389.2; 530/389.7
(58) Field of Search .......................... 424/158.1, 145.1, 424/130.1, 133.1, 156.1; 530/389.2, 387.1, 388.24, 388.85, 389.1, 389.7

(56) References Cited

U.S. PATENT DOCUMENTS

| | | |
|---|---|---|
| 4,061,767 | 12/1977 | Ertel et al. . |
| 4,381,295 | 4/1983 | Kung et al. . |
| 4,603,106 | 7/1986 | Cerami et al. . |
| 4,684,623 | 8/1987 | Larrick et al. . |
| 4,731,244 | 3/1988 | Talle et al. . |
| 4,742,159 | 5/1988 | Batz et al. . |
| 4,822,776 | 4/1989 | Cerami et al. . |
| 4,849,352 | 7/1989 | Sullivan et al. . |
| 4,870,163 | 9/1989 | Rubin et al. . |
| 4,879,226 | 11/1989 | Wallace et al. . |
| 4,918,163 | 4/1990 | Young et al. . |
| 5,124,147 | 6/1992 | Wissner et al. . |
| 5,183,657 | * 2/1993 | Buurman ............................ 424/85.8 |
| 5,436,154 | * 7/1995 | Barbanti et al. ................ 435/240.27 |
| 5,656,272 | 8/1997 | Le et al. . |
| 5,672,347 | * 9/1997 | Aggarwal et al. . |
| 5,795,967 | * 8/1998 | Aggarwal et al. . |

FOREIGN PATENT DOCUMENTS

| | | |
|---|---|---|
| 660660 | 10/1992 | (AU) . |
| 131836 | 1/1985 | (EP) . |
| 0 143 413 A3 | 6/1985 | (EP) . |
| 0 212 489 | 3/1987 | (EP) . |
| 0 350 690 A2 | 1/1990 | (EP) . |
| 0 351 789 A2 | 1/1990 | (EP) . |
| 0 355 067 A1 | 2/1990 | (EP) . |
| 0 387 095 | 9/1990 | (EP) . |
| 0 460 426 A2 | 12/1991 | (EP) . |
| WO83/00930 | 3/1983 | (WO) . |
| WO84/03712 | 9/1984 | (WO) . |
| WO 88/02594 | 4/1988 | (WO) . |
| WO 89/08460 | 9/1989 | (WO) . |
| WO 90/10707 | 9/1990 | (WO) . |
| 91/02078 | * 2/1991 | (WO) . |
| WO 91/01755 | 2/1991 | (WO) . |
| WO 91/07986 | 6/1991 | (WO) . |
| WO 92/07585 | 5/1992 | (WO) . |
| WO 92/16553 | 10/1992 | (WO) . |
| WO93/02108 | 2/1993 | (WO) . |
| WO 93/11793 | 6/1993 | (WO) . |
| WO94/08619 | 4/1994 | (WO) . |
| WO94/10980 | 5/1994 | (WO) . |
| WO 94 29347 | 12/1994 | (WO) . |
| WO 94 29348 | 12/1994 | (WO) . |
| 895325 | 7/1989 | (ZA) . |

OTHER PUBLICATIONS

Schlom, Molecular Foundations of Oncology Samuel Broder ed. 1991, p. 95.*
Tracey et al. Nature vol. 330, 1987 p. 662.*
Socher, Susan H., et al, "Antibodies against amino acids 1–15 of tumor necrosis factor block its binding to cell–surface receptor," *Proc. Natl. Acad. Sci USA*, vol. 84, pp. 8829–33 (Dec. 1987).
Beutler, Bruce, et al., "The History, Properties, and Biological Effects of Cachectin," *Biochem.*, vol. 27, No. 20 pp. 7575–7582 (Oct. 4, 1988).
Evans, Rhys D., et al., "Metabolic effects of tumour necrosis factor–α (cachectin) and interleukin–1," *Clin.Sci.* vol. 77, pp. 357–364 (1989).
Remick, Daniel G., et al., "Acute in Vivo Effects of Human Recombinant Tumor Necrosis Factor," *Laboratory Investigation*, vol. 56, No. 6, p. 583 (1987).
Fendly, Brian M., et al., "Murine Monoclonal Antibodies Defining Neutralizing Epitopes on Tumor Necrosis Factor," *Hybridoma*, vol. 6, No. 4, pp. 359–370 (1987).
Fong, Yuman, et al., "Antibodies to Cachectin/Tumor Necrosis Factor Reduce Interleukin 1β and Interleukin 6 Appearance During Lethal Bacteremia," *J. Exp. Med.*, vol. 170, pp. 1627–1633 (Nov. 1989).
Pennica, Diane, et al., "Human tumour necrosis factor: precursor structure, expression and homology to lymphotoxin," *Nature*, vol. 312, No. 20/27, pp. 724–729 (Dec. 1984).
Aggarwal, Bharat B., et al., "Human Tumor Necrosis Factor," *J. Biol. Chem.*, vol. 260, No. 4, pp. 2345–2354 (Feb. 25, 1985).

(List continued on next page.)

Primary Examiner—Julie Burke
Assistant Examiner—Larry R Helms
(74) *Attorney, Agent, or Firm*—Finnegan, Henderson, Farabow, Garrett & Dunner, L.L.P.

(57) ABSTRACT

A method of neutralizing TNFα in a patient benefiting from such neutralizing, comprising administering to the patient IgG Fab fragment reactive towards TNFα. Suitably, the patient is suffering from septic shock or from the symptoms of septic shock. It is preferred if the Fab fragment is derived from polyclonal IgG.

14 Claims, 9 Drawing Sheets

OTHER PUBLICATIONS

Beutler, B., et al., "Passive Immunization Against Cachetin/Tumor Necrosis Factor Protects Mice form Lethal Effect of Endotoxin," *Science*, vol. 229, pp. 869–871 (Aug. 30, 1985).

Beutler, B., et al., "Cachectin and tumour necrosis factor as two sides of the same biological coin," *Nature*, vol. 320, pp. 584–588 (Apr. 17, 1986).

Mannel, Daniela N., et al., "Macrophages as a Source of Tumoricidal Activity (Tumor Necrotizing Factor)," *Inf. & Immun.*, vol. 30, No. 2, pp. 523–530 (Nov. 1980).

Haidaris, Constantine G., et al., "Serum Containing Tumor Necrosis Factor is Cytotoxic for the Human Malaria Parasite *Plasmodium falciparum,*" *Inf. and Immun.*, vol. 42, No. 1, pp. 385–393 (Oct. 1983).

Kengatharan et al., "Polyclonal antibodies against TNF–α and IL–1β prevent the circulatory failure elicited by lipoteichoic acid in anaesthetised rats," British J. of Pharmacology 116:66P (1995).

Zhang et al., "Enhanced Interleukin–8 Release and gene expression in macrophages after exposure to *Mycobacterium tuberculosis* and its components," J. Clin. Invest. 95(2):586–592 (1995).

Issekutz et al., "The role of tumour necrosis factor–alpha and IL–1 in polymorphonuclear leucocyte and T lymphocyte recruitment to joint inflammation in adjuvant arthritis," Clin. Exp. Immunol. 97:26–32 (1994).

Textbook of Medical Physiology. Guyton. Saunders co. pp. 380–381, 1981.*

Aggarwal et al. Human Tumor Necrosis Factor Production, Purification, and Characterization, Journal of Biological Chemistry, vol. 260, No. 4, pp. 2345–2354, Aug. 21, 1984.

Beutler et al., Purification of Cachectin, A Lipoprotein Lipase–Suppressing Hormone Secreted by Endotoxin–Induced Raw 264.7 Cells, J. Exp. Med., vol. 161, pp. 984–995, May, 1985.

Beutler et al., Identity of Tumour Necrosis Factor and the Macrophage–Secreted Factor Cachectin, Nature, vol. 316, pp. 552–554 Aug., 8, 1985.

Beutler et al., Cachectin and Tumour Necrosis Factor as Two Sides of the Same Biological Coin, Nature, vol. 320, pp. 584–588 Apr. 17, 1986.

Beutler et al., Passive Immunization Against Cachectin/Tumor Necrosis Factor Protects Mice From Lethal Effect of Endotoxin, Science, vol. 229, pp. 869–871, Aug. 30, 1985.

Beutler et al., Fed. Proc. 44, 1704, Activated Macrophages Secrete A Novel Lipolytic Polypeptide Hormone, Abstract No. 7565, 1985.

Bone, A Critical Evaluation of New Agents for the Treatment of Sepsis, JAMA, vol. 266, No. 12, pp. 1686–1691, Sep. 25, 1991.

Buttle et al., The Preparation of Fully Active Chymopapain Free of Contaminating Proteinases, Biol. Chem. Hoppe–Seyler, vol. 371, pp. 1083–1088, Nov., 1990.

Buttle et al., Affinity Purification of the Novel Cysteine Proteinase Papaya Proteinase IV, and Papain from Papaya Latex, Biochem J., vol. 261, pp. 469–476, 1989.

Brennan et al., Inhibitory Effect of TNFα Antibodies on Synovial Cell Interleukin–1 Production in Rheumatoid Arthritis, The Lancet, pp. 244–247, Jul. 29, 1989.

Carswell et al., An Endotoxin–Induced Serum Factor that Causes Necrosis of Tumors, Proc. Nat. Acad. Sci., vol. 72, No. 9, pp. 3666–3670, Sep., 1975.

Cerami et al., Weight Loss Associated with an Endotoxin–Induced Mediator from Perintoneal Macrophages: The Role of Cachectin (Tumor Necrosis Factor), Immunology Letters, vol. 11, pp. 173–177, 1985.

Elliott et al., Treatment of Rheumatoid Arthritis with Chimeric Monoclonal Antibodies to Tumor Necrosis Factorα, Arthritis & Rheumatism, vol. 36, No. 12, pp. 1681–1690, Dec., 1993.

Erikaku et al., Bioluminescent Immunoassay Using a Monomeric Fab'–Photoprotein Aequorin Conjugate, Biochemical and Biophysical Research Communications, vol. 174, No. 3, pp. 1331–1336, Feb. 14, 1991.

Feldmann et al., Evaluation of the Role of Cytokines in Autoimmune Disease: The Importance of TNFα in Rheumatoid Arthritis, Progress in Growth Factor Research, vol. 4, pp. 247–255, 1992.

Fransen et al., Molecular Cloning of Mouse Tumour Necrosis Factor cDNA and its Eukaryotic Expression, Nucleic Acids Research, vol. 13, No. 12, pp. 4417–4429, 1985.

Glauser et al., Septic Shock: Pathogenesis, The Lancet, vol. 338, p. 732–736, Sep. 21, 1991.

Goldstein et al., A Randomized Clinical Trial of OKT3 Monoclonal Antibody for Acute Rejection of Cadaveric Renal Transplants, The New England Journal of Medicine, vol. 313, No. 6, pp. 337–342, Aug. 8, 1985.

Haranaka et al., Purification and Partial Amino Acid Sequence of Rabbit Tumor Necrosis Factor, Int. J. Cancer, vol. 36, pp. 395–400, 1985.

Hinds, Monoclonal Antibodies in Sepsis and Septic Shock, BMJ, vol. 304, pp. 132–133, Jan. 18, 1992.

Hotez et al., Lipoprotein Lipase Suppression in 3T3–L1 Cells by a Haematoprotozoan–Induced Mediator from Peritoneal Exudate Cells, Parasite Immunology, vol. 6, pp. 203–209, 1984.

Lamoyi et al., Preparation of F(ab')₂ Fragments from Mouse IgG of Various Subclasses, Journal of Immunological Methods, vol. 56, No. 2, pp. 235–243, Jan. 28, 1983.

Kawakami et al., Lipoprotein Lipase Suppression in 3T3–L1 Cells by an Endotoxin–Induced Mediator from Exudate Cells, Proc. Natl. Acad. Sci., vol. 79, pp. 912–916, Feb., 1982.

Kawakami et al., Studies of Endotoxin–Induced Decrease in Lipoprotein Lipase Activity, J. Exp. Med., vol. 154, pp. 631–639, Sep., 1981.

Liang et al., Production and Characterization of Monoclonal Antibodies Against Recombinant Human Tumor Necrosis Factor/Cachectin, Biochemical and Biophysical Research Communications, vol. 137, No. 2, pp. 847–854, 1986.

Mahoney, Jr., et al., Lipopolysaccharide–Treated Raw 264.7 Cells Produce a Mediator that Inhibits Lipoprotein Lipase in 3T3–L1 Cells, The Journal of Immunology, vol. 134, No. 3, pp. 1673–1675, Mar., 1985.

Maini et al., TNF–α in Rheumatoid Arthritis and Prospects of Anti–TNF Therapy, Clinical and Experimental Rheumatology 11, Suppl. 8: pp. S173–S175, 1993.

Mannel et al., Macrophages as a Source of Tumoricidal Activity (Tumor–Necrotizing Factor), Infection and Immunity, vol. 30, No. 2, pp. 523–530, Nov., 1980.

Mannel et al., Inhibition of Nonspecific Tumoricidal Activity by Activated Macrophages with Antiserum Against a Soluble Cytotoxic Factor, Infection and Immunity, vol. 33, No. 1, pp. 156–164, Jul., 1981.

Nawa, Tissue–specific Generation of Two Preprotachykinin mRNAs from One Gene by Alternative RNA Splicing, Nature vol. 312, 20/27, pp. 729–734, Dec., 1984.

Negussie et al., Detection of Plasma Tumor Necrosis Factor, Interleukins 6, and 8 during the Jarisch–Herxheimer Reaction of Relapsing Fever, J. Exp. Med., vol. 175, pp. 1207–1212, May, 1992.

Pekala et al., Selective Inhibition of Synthesis of Enzymes for de novo Fatty Acid Bio–Synthesis by an Endotoxin–Induced Mediator from Exudate Cells, Proc. Natl. Acad. Sci., vol. 80, pp. 2743–2747, May, 1983.

Pennica et al., Human Tumour Necrosis Factor: Precursor Structure, Expression and Homology to Lymphotoxin, Nature, vol. 312, 20/27, pp. 724–729, Dec., 1984.

Piquet et al., Evolution of Collagen Arthritis in Mice is Arrested by Treatment with Anti–Tumour Necrosis Factor (TNF) Antibody or a Recombinant Soluble TNF Receptor, Immunology, vol. 77, pp. 510–514, 1992.

Rouzer et al., Hypertriglyceridemia Associated with Trypanosoma Brucei Brucei Infection in Rabbits: Role of Defective Triglyceride Removal, Molecular and Biochemical Parasitology, vol. 2, pp. 31–38, 1980.

Schnabel, The Magic Bullet that Burst the Bubble, New Scientist, Sep. 26, 1992, pp. 31–35.

Shim et al., The Nature of Endotoxin–Induced Tumor Necrosis Factor, Korean J. Biochem., vol. 11, pp. 1–9, 1979.

Smith et al., An Affinity Purified Ovine Antivenom for the Treatment of *Vipera Berus* Envenoming, Toxicon, vol. 30, No. 8, pp. 865–871, 1992.

Teng et al., Protection Against Gram–Negative Bacteremia and Endotoxemia with Human Monoclonal IgM Antibodies, Proc. Natl. Acad. Sci., vol. 82, pp. 1790–1794, Mar., 1985.

Tracey et al., Anti–Cachectin/TNF Monoclonal Antibodies Prevent Septic Shock during Lethal Bacteraemia, Nature, vol. 330, pp. 662–664, Dec., 1987.

Williams et al., Anti–Tumor Necrosis Factor Ameliorates Joint Disease in Murine Collagen–Induced Arthritis, Proc. Natl. Acad. Sci., vol. 89, pp. 9784–9788, Oct. 1992.

Williamson et al., Human Tumor Necrosis Factor Produced by Human B–Cell Lines: Synergistic Cytotoxic Interaction with Human Interferon, Proc. Natl. Acad. Sci., vol. 80, pp. 5397–5401, Sep., 1983.

Ziegler, Treatment to Gram–Negative Bacteremia and Shock with Human Antiserum to a Mutant *Escherichia Coli*, The New England Journal of Medicine, vol. 307, No. 20, pp. 1225–1230, Nov. 11, 1982.

SCRIP No. 1818/19, Celltech Completes Anti–TNF Study, Products Articles, PJB Publications Ltd., May 7/11, 1993.

SCRIP No. 1843, Centocor's Anti–TNF $MA_b$ for Crohn's Disease, Products Articles, PJB Publications Ltd. Aug. 3, 1993.

Raikher et al., Isolation of Fab– and Fc–Fragments of Immunoglobulins Without Column Chromatography, Chemical Abstracts, vol. 102, No. 5, Abstract No. 43971j, Feb. 4, 1985.

* cited by examiner

ANTIBODY FRAGMENTS IN THERAPY

The present invention relates to the use of immunoglobulin Fab fragments in therapy.

Antibodies are formed as part of the immune response to a microorganism or foreign macromolecule. They are immunoglobulins (Ig) and are used extensively in clinical practice for the diagnosis, monitoring, prevention and treatment of an increasing number of diseases.

Figure 1:
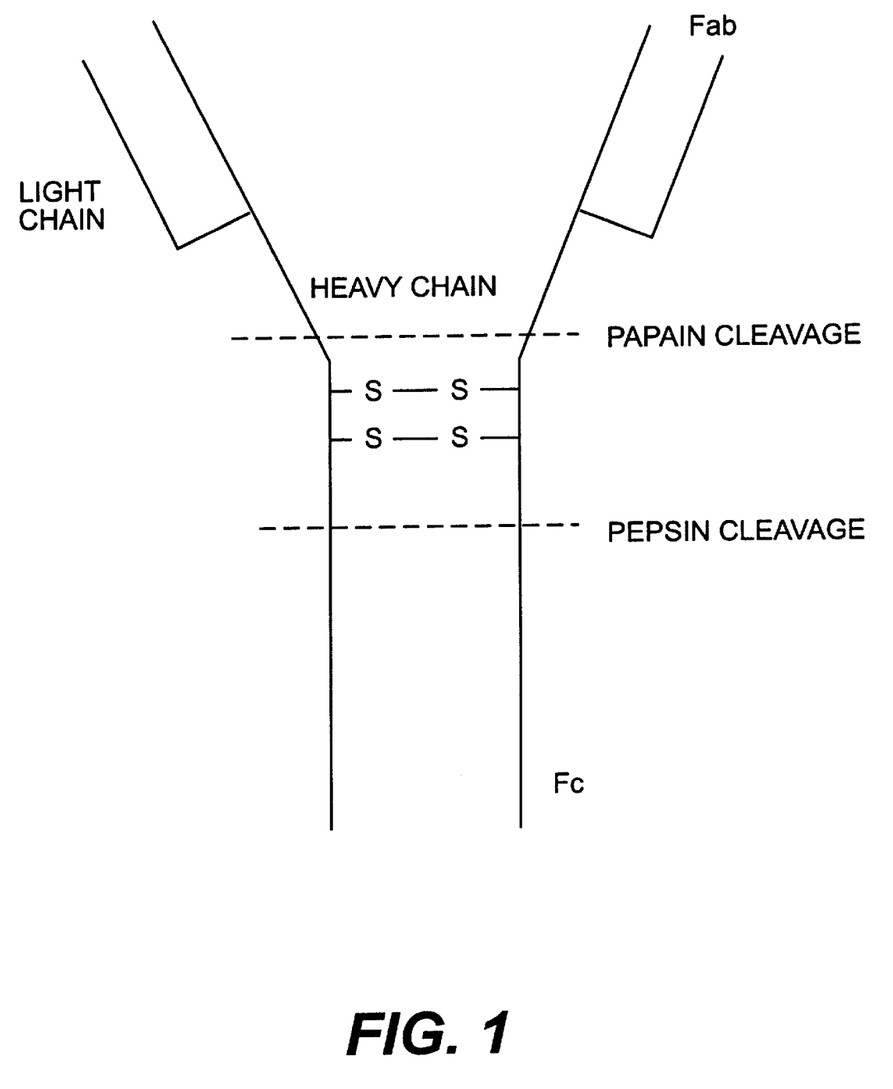
FIG. 1 is a diagrammatic representation of the structure of an antibody molecule.

The basic unit from which all antibody molecules are formed was elucidated by Porter (1959) *Biochem J*. 73, 119–126, using specific proteolytic enzymes. The most important of the immunoglobulins, IgG, comprises two heavy and two light chains with the former being coupled at their hinge region by disulphide linkages. Cleavage with papain above these linkages releases two antibody binding fragments (Fab) and a crystalline fragment (Fc) as shown in FIG. 1. Cleavage with pepsin, below the hinge results in a somewhat smaller Fc fragment and a single F(ab')$_2$ fragment with two binding sites as shown in FIG. 1. Each Fab fragment contains both a light chain and part of a heavy chain, and includes the sequences responsible for specific binding to a microorganism or foreign macromolecule. The Fc consists of the remainder of the two heavy chains; this is the site to which complement, macrophages and polymorphonuclear white blood cells can bind. The two heavy chains (but not the light chains) are different for each class of antibody ie IgG, IgM, IgA and IgE. IgG is the dominant circulating immunoglobulin in terms of concentration. It consists of a single basic immunoglobulin unit and, characteristically, has a high affinity for its specific antigen. Further details of antibody structure and function are disclosed in Roitt (1991) *Essential Immunology*, 7th Edition, Blackwell Scientific Publications, Oxford.

Microbial pathogens can cause deleterious effects by releasing soluble toxins. These include the neurogenic exotoxins released by diphtheria and tetanus bacilli and various endotoxins such as lipopolysaccharide (LPS) from the cell walls of Gram-negative bacteria and peptidoglycans from Gram-positive organisms. In 1890 von Behring showed that exogenous antibodies to soluble antigens were of therapeutic value: the mortality of children with diphtheria was reduced by systemic administration of serum from horses hyperimmunised with diphtheria toxoid. A similar approach was successful in patients with tetanus. Passive immunisation was quickly extended to the victims of snake envenomation by Calmette in 1894, and by others.

The development of the septic shock syndrome involves initiators (such as LPS), mediators (including TNFα, IL-1 and IL-6) and effectors at the cellular level (eg nitric oxide synthase in endothelial cells). An the initiators and mediators are potential antigens; antibodies against these macromolecules can be used for the prevention and treatment of septic shock. Several groups have used polyclonal (PcAb) or monoclonal antibodies (McAb) directed against LPS with varying degrees of success. At the same time, it has been shown that PcAb to TNFα can prevent the lethal effects of this cytokine (Beutler et al (1985) *Science* 229, 869–871) in BALB/C mice. Tracey and colleagues ((1987) *Nature* 330, 662–664) have shown that McAb against TNFα given one hour before bacterial challenge in baboons afforded partial protection against organ damage and, when given two hours before, more complete protection. In other words the anti-TNFα McAb was used prophylactically.

A few groups have raised PcAb to LPS and to TNF, usually in rabbits, and demonstrated their effectiveness in animal models of septic shock. PcAb to LPS have also been raised in human volunteers and used successfully (Ziegler et al (1982) *New Engl. J. Med*. 307, 1225–1230). Although the use of human antibodies avoids the risk of allergic complications, widespread application is precluded by ethical, logistic and other reasons including potential for viral contamination (HIV and hepatitis). Therefore most groups have concentrated their efforts on the production of McAB. McAb offer many advantages, for example homogeneity and the relative simplicity of down-stream processing—often by affinity chromatography with protein A or protein G to separate antibodies from other proteins.

No group involved in developing treatments for septic shock have prepared or used specific Fab fragments. No group has demonstrated the use of anti-TNF Fab fragments in treating humans suffering from septic shock after clinical manifestations of the shock have become apparent.

SUMMARY OF THE INVENTION

We have now demonstrated in humans that administration of Fab fragment reactive towards TNFα benefits patients suffering from "septic shock" symptoms.

We have unexpectedly found that Fab fragments, derived from polyclonal antibodies directed towards TNFα, are more effective at reducing the effects of TNF than are intact IgG directed towards TNFα as disclosed in more detail in the Examples.

Thus, one aspect of the invention provides a method of neutralising TNFα in a patient benefiting from such neutralising, comprising administering to the patient Fab fragment reactive towards TNFα.

Suitably, the patient is suffering from septic shock or from the symptoms of septic shock. Thus, a further aspect of the invention provides a method of preventing or ameliorating septic shock or the symptoms of septic shock in a patient comprising administering to the patient IgG Fab fragments reactive towards TNFα.

The Fab fragments may be generated from substantially pure IgG reactive towards TNFα by methods well known in the art and disclosed in the Examples.

A further aspect of the invention provides IgG Fab fragments reactive towards TNFα for use in medicine.

A still further aspect of the invention provides use of an IgG Fab fragment reactive towards TNFα in the manufacture of a medicament for treating patients benefiting from neutralisation of TNFα.

It is further preferred if the IgG Fab fragments are derived from polyclonal antiserum. Polyclonal antiserum (which includes polyclonal IgG) can be produced by immunizing a sheep, goat, horse or other mammal. It is preferable if the mammal is a sheep, and that it is free of scrapie and zoonotic viruses. Methods of making Fab fragments reactive towards TNFα and derived from polyclonal sheep IgG are described in the Examples.

Fab fragments reactive towards TNFα are useful in the treatment of medical conditions characterised by an increase in the level of circulating TNFα. Such conditions include shock, for example septic shock, and excess TNFα in the context of tumour therapy. Septic shock may occur following bacterial infection, particularly infection with Gram-negative bacteria, and during septicaemia. By shock we also include trauma following an accident or surgery. Further uses include treatment in conjunction with anti-lymphocyte antibody therapy, as taught in WO 89/08460, and in conjunction with cancer chemotherapy, as taught in EP 355 067.

It is known that intravenous infusions of laprine or equine polyclonal antibodies directed against human lymphocytes are very effective in helping to treat acute renal allograft rejection. Such products are still in use. Following clinical trials, Ortho Pharmaceutical Co was granted a licence by the FDA in 1986 for the routine use of a murine monoclonal antibody, OKT3, to help to prevent graft rejection following renal transplant. This product has proved extremely effective in the treatment of acute rejection episodes following kidney, liver and heart transplants and OKT3 remains the only monoclonal-based therapeutic product to have been granted a licence.

OKT3 binds specifically to the CD-3 complex found on all mature T lymphocytes. CD-3 is normally involved in antigen recognition and cell stimulation and both are prevented, due to steric hindrance, by the presence of the murine antibodies.

The hybridoma expressing the monoclonal antibody OKT3 is available from the America Type Culture Collection, 12301 Parklawn Drive, Rockville, Md. 20852 U.S.A. under accession number ATCC CRL 8001. It is of the IgG2a isotype and reactive to human helper T cell subset. The hydridoma and antibody are cited in U.S. Pat. No. 4,381,295 incorporated herein by reference. A treatment regime with OKT3 is described in Ortho Study Group (1985) N. Engl. J. Med. 313, 337–342 incorporated herein by reference.

However, patients have a price to pay, in terms of side-effects, for the undoubted benefits which accrue from such anti-T-lymphocyte therapy. Thus during the first infusion of a polyclonal anti-lymphocyte globulin and following the first injection of OKT3, virtually every patient experiences severe signs and symptoms. These include fever in at least 90% of subjects, headaches, nausea and vomiting, diarrhoea, general malaise and extreme fatigue, dyspnoea, myalgia and tachycardia. A few patients develop acute pulmonary oedema. During the second period of therapy side-effects are minimal and, during all subsequent periods, non-existent.

These clinical manifestations are similar to those encountered following infusions of TNF or in septic shock. Infusions of anti-lymphocyte globulin have been shown to cause a marked increase in circulating TNF from undetectable levels to values ranging from 111 to 731 ng/L, without interleukin-1beta (IL-1β) being measurable. This rise in TNF is closely followed by fever (from 38.4 to 40.4° C.).

It is an object of the present invention to reduce the shock-like symptoms following OKT3 or anti-lymphocyte globulin treatment.

Thus, in one preferred embodiment the IgG Fab fragment reactive towards TNFα is used to treat patients who are receiving the monoclonal antibody OKT3, or functionally equivalent polyclonal antisera, for example in order to reduce actue rejection during kidney transplantation. The IgG or Fab fragment reactive against TNFα reduces the shock-like side effects of the treatment with OKT3 or functionally equivalent antibodies.

Louse-borne relapsing fever (LBRF), caused by the spirochaete *Borrelia recurrentis*, has been responsible for massive pandemics in Europe, Africa and the Middle East during this century but it is currently restricted to an endemic focus in the highlands of Ethiopia. During epidemics the mortality of the untreated disease may exceed 40% but is reduced to less than 5% with antimicrobial agents including penicillin, tetracyclines, chloramphenicol and erythromycin. Clinical cure, can only be achieved by the use of antibiotics which induce a violent and sometimes fatal Jarisch-Herxheimer reaction (JHR). Intravenous tetracylcines cause such a reaction which starts predictably within about an hour of treatment and consists of three phases-rigors, flush and deferverscence-of the classical "endotoxin" or "shock" reaction (Warrell et al (1970) Clin. Sci. 39, 123–145. Patients may die during the reaction, either with hyperpyrexia at the peak of the fever during the early part of the flush phase, or of shock or acute myocardial failure during the flush/deferverscence phase.

Negussie and his colleagues ((1992) J. Exp. Med. 175, 1203–1207) documented the explosive release of TNFα, followed by IL-6 and IL-8 during this JHR.

Thus, in a further embodiment IgG Fab fragments reactive towards TNFα are used to treat patients with symptoms of septic shock as evidenced by the Jarisch-Herxheimer reaction.

Suitably the JHR is associated with the antibiotic treatment of louse-borne-relapsing fever.

It is well known that JHR, or a similar reaction, is associated with antibiotic treatment of various other parasitic and invading organism diseases including syphilis, tick-borne relapsing fever, Vincent's angina, rat-bite fever, leptospirosis, yaws, brucellosis and African trypanosomiasis.

It will be appreciated that the treatment of the symptoms associated with the antibiotic treatment of LBRF using anti-TNF Fab as described in the Examples will also be used to treat the JHR or similar reaction associated with the antibiotic treatment of the abovementioned diseases.

It will be further appreciated that the JHR of louse-borne relapsing fever provides an ethical model for clinical testing of anti-TNFα intervention, and that it is well known that an increase in the levels of TNFα is found in JHR.

A further aspect of the invention provides a pharmaceutical composition comprising IgG Fab fragments reactive towards TNFα and a physiologically tolerable carrier.

In general, the IgG Fab fragments may be used whenever one wishes to neutralise TNFα in a patient. The dose administered will be determined by reference to the weight of the patient and the severity of the condition but, typically, 200–2000 mg of specific anti-TNFα Fab fragment will be administered to an adult over 2 to 3 days.

Conveniently, when the Fab fragment is derived from polyclonal antisera and is not affinity purified, 120 mg/kg of total Fab is administered which contains about 20 mg/kg of specific anti-TNFα Fab.

It is preferred if the Fab fragment is substantially pure and is non-pyrogenic. Fab fragment can be substantially purified using chromatographic techniques such as cation exchange chromatography or affinity chromatography. Preferably the Fab fragment is affinity purified.

The IgG Fab fragments of the invention or a formulation thereof may be administered by any conventional systemic method including parenteral (eg intravenous, subcutaneous or intramuscular) injection. The treatment may consist of a single dose or a plurality of doses over a period of time.

Whereas it is possible for the IgG Fab fragment of the invention to be administered alone, it is preferable to present it as a pharmaceutical formulation, together with one or more acceptable carriers. The carrier(s) must be "acceptable" in the sense of being compatible with the Fab fragment and not deleterious to the recipients thereof.

Formulations of the IgG Fab fragments may conveniently be presented in unit dosage form and may be prepared by any of the methods well known in the art of pharmacy. Such methods include the step of bringing into association the IgG Fab fragment with the carrier which constitutes one or more accessory ingredients. In general the formulations are prepared by uniformly and intimately bringing into association the active ingredient with liquid carriers.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared. Preferred unit dosage formulations are those containing a daily dose or unit, daily sub-dose or an appropriate fraction thereof, of an active ingredient.

The invention will now be described with reference to the following Examples and Figures wherein

EXAMPLE 1

Preparation of TNFα Immunogen for Immunizing Sheep

Procedure
Preparation of vials containing active TNFα immunogen

The vials should be new, dust free and treated with sialinating fluid 48 hours in advance to prevent adhesion of the immunogen to the vials. Fresh sialinating solution needs to be made up every 24 hours.

Sialinating is carried out in the following way:

a) In a fume hood line up vials in a metal tray;

b) Make up sialinating solution to the manufacturer's instructions. Dilute to a 0.1% solution. Note 0.2% solution is achieved by 99 parts water to 1 part AQUA-SIL (Trademark). Stir constantly. Flood the vials in the solution. Then allow to air dry for a minimum of 24 hours.

Remove TNFα from the 4° C. store and allow to equilibrate at room temperature for a minimum of 30 minutes.

The total amount of TNFα for a single monthly immunization for the entire flock is weighed out into a sterile 150 ml Sterilin (Trademark) flask using the balance. The necessary calculations are given under the heading "Calculations involved in immunogen preparation" below. This is represented as E in the calculations described below. Any spare immunogen prepared may be stored and used at a later date.

The immunogen is then dissolved in 0.9% saline. The solution is then mixed by end-over-end rotation for a minimum of 30 minutes. The amount of saline used is F as described below.

The prepared immunogen solution is aliquoted into vials using sterile pipettes and a Pipetteman (Trademark) device.
Calculations Involved in the Immunogen Preparation Each vial should contain sufficient immunogen for 3 sheep. Therefore divide the total number of sheep for immunization (A) by three and round up to the next whole number.

$$A/3=B$$

eg 49/3=16.33 therefore 17

The amount of TNFα to be weighed out is therefore 3B multiplied by the amount of immunogen needed per sheep (C).

$$(3*B)C=D$$

eg If preparing immunizing dose of 80 μg per sheep (3*17)80=4080 μg=4.08 mg

The amount of TNFα compared with the salt content, which can vary from batch to batch, has to be taken into account when weighing immunogen.

$$(D/\text{percentage TNF}\alpha \text{ in supplied material})100=E$$

eg If the supplied material contains 95% salt and therefore 5% TNFα (4.08/5)100=81.6 mg The weighed out immunogen is then dissolved in the appropriate amount of 0.9% saline, which is calculated by multiplying the number of vials to be used by 4. Each vial should contain 4 ml of saline.

$$B*4=F$$

eg 17*4=68 ml

EXAMPLE 2

Immunization, Sample and Bleed Protocol for Anti-TNFα Sheep

The table gives a year's fortnightly schedule of the immunization dose administered, the volume of bleed and the processing of individual samples or pooled samples for the production sheep immunized against TNFα.

A sample is taken from each animal prior to primary immunization. This level is the background level in each sheep.

The following definitions are used:

| | |
|---|---|
| I: | Primary Immunization |
| R#: | Reimmunization number post primary immunization |
| Sample: | 5–10 ml blood sample from each animal for assessment of titre |
| Bleed: | 10 ml blood taken per kg of body weight |
| IS: | Individual sample for assessment of the individual performance |
| P: | Pooling of bleeds from all individuals |

| Week Number | Immunization Number | Dose (μg) | Sample or Bleed | Sample Processing |
|---|---|---|---|---|
| 0 | I | 160 | | |
| 2 | | | | |
| 4 | R1 | 80 | | |
| 6 | | | Sample | IS |
| 8 | R2 | 80 | | |
| 10 | | | | |
| 12 | R3 | 80 | | |
| 14 | | | | |
| 16 | R4 | 80 | | |
| 18 | | | | |
| 20 | R5 | 80 | | |
| 22 | | | Sample | IS |
| 24 | R6 | 80 | | |
| 26 | | | Bleed | P |
| 28 | R7 | 80 | | |
| 30 | | | Bleed | P |
| 32 | R8 | 80 | | |
| 34 | | | Bleed | P |
| 36 | R9 | 80 | | |
| 38 | | | Bleed | P |
| 40 | R10 | 80 | | |
| 42 | | | Bleed | P |
| 44 | R11 | 80 | | |
| 46 | | | Bleed | P |
| 48 | R12 | 80 | | |
| 50 | | | Bleed | P |
| 52 | R13 | 80 | | |

EXAMPLE 3

Preparation of Anti-TNFα Fab Fragments From Partially Purified IgG

Sheep are immunised according to a set schedule with amounts of rhTNFα selected on the basis of dose response studies and as disclosed in Examples 1 and 2. Once adequate circulating specific antibody levels have been obtained (at least 3 g/L) the sheep are bled aseptically into sterile and pyrogen-free glass bottles; clotting is accelerated by use of a roll-bottle technique; the bottles are centrifuged; and the serum is collected by aspiration in a laminar flow cabinet, subjected to 0.2 μm filtration and stored at −20° C. Bacterial and pyrogen contamination is prevented and the product is subjected to rigorous quality control.

Antisera from different animals are pooled and their immunoglobulins precipitated at 25° C. with sodium sulphate to separate them from most other serum proteins including albumin. The immunoglobulins, which largely comprise antibodies of the IgG class, are washed with sterile sodium sulphate and resuspended in saline.

Papain digestion: The next step is cleavage of the antibodies into Fab and Fc using papain activated with cysteine and EDTA. This is carried out under conditions that ensure the complete degradation of intact IgG. The crystalline Fc is removed by centrifugation. The supernatant after papain digestion and centrifugation will contain: (1) specific Fab directed against the soluble antigen of interest; (2) non-specific Fab directed against numerous other epitopes and of no value for therapy; (3) small amounts of protein (including albumin) and other contaminants; and (4) inactivated papain.

Affinity Chromatography

Affinity Purification. Affinity purification of human tumour necrosis factor (anti-TNF) Fab fragment is performed using a cross-linked agarose (Sepharose) medium to which rTNFα (recombinant human TNFα) has been bound. An iso-urea linkage is used to couple the rTNFα to the medium.

Manufacture of Agarose-rTNFα Affinity Column Matrices

Materials

Cyanogen bromide activated Sepharose 4B (Pharmacia, Uppsala, Sweden)

rTNFα (R/D Systems Minneapolis, U.S.A.)

BPG affinity column housing (Pharmacia)

Large glass sinter funnel

Buchner flask

Vacuum pump

Glass rod

Nalgene bottle

Buffers and Solutions

All buffers must be sterile and pyrogen free (see SOP 0.2, preparation of sterile, non-pyrogenic buffers for therapeutic manufacture).

Hydrochloric Acid (1 mM, 200 ml/g, ice cold)

Sodium bicarbonate (0.1M, pH 8.3) containing sodium chloride (0.5M)

Ethanolamine (1.0M, pH 8.0)

Sodium acetate (0.1M, pH 4.0) containing sodium chloride (0.5M)

Procedure. When making columns for therapeutic manufacture, all procedures should be performed under laminar flow in class 100 conditions and all equipment should be sterile and pyrogen free.

Swelling and washing the gel: the required amount of freeze-dried Sepharose powder should be weighed out into a plastic Nalgene bottle and suspended in HCl (ice cold). The gel swells immediately and should be washed for 15 minutes on a sintered glass filter with the same solution (200 ml/g of gel). The solution should be added in several aliquots and the gel should be dried, after the final aliquot, until cracks appear in the surface.

Coupling the ligand: the TNF ligand (5 mg/g of gel to be used) should be dissolved in sodium bicarbonate buffer (0.1M, pH 8.3, 7 ml/g of gel to be used) in a plastic Nalgene bottle. Once dissolved, an aliquot (0.25% of the total) should be taken and then the air dried gel should be added, taking care not to splash the ligand solution from the bottle. The mixture should then be rotated, end over end, at 4° C. overnight.

Blocking the active groups on the gel: after coupling overnight, the gel solution should be transferred back to the glass sinter funnel and the ligand solution aspirated and collected. The gel should then be washed with 200 ml of ethanolamine. All washings should be collected.

The gel should then be transferred to a Nalgene bottle containing ethanolamine (1.0M, pH 8.0) and the mixture rotated overnight as before.

Washing the gel: the blocked gel should be transferred to the sinter funnel and the ethanolamine solution sucked off and collected. The gel should then be washed with coupling buffer (bicarbonate) followed by acetate buffer, then coupling buffer a second time. All washings should be collected.

The gel may now be transferred and packed into the column housing and washed thoroughly with saline (0.9%).

The coupling efficiency should be determined by measuring the amount of protein in the washings and comparing this with the initial ligand solution aliquot.

Columns are sanitised using guanidinium hydrochloride (6.0M) after each batch of material is completed and prior to the first addition of total Fab digest solution.

The Fab solution is circulated at a flow rate of 1 ml/minute for a minimum of two hours at 18° C.

Desorption of the rTNFα antitoxin Fab from the affinity support.

The ovine rTNFα Fab fragment bound to the support is removed by washing the column with glycine (10 mM, pH 2.5). The eluant is collected into citrate buffer (0.6M, pH 8.0:2.5% final concentration) and stored in Nalgene, 2 liter disposable collection bottles. Samples are taken for QC testing (GF FPLC, pH, protein concentration, sterility and LAL testing).

Affinity columns are re-equilibrated using phosphate buffer (10 mM, pH 7.3) until the eluant pH returns to approximately pH 5.5. The column is then equilibrated with saline (0.9%) to prepare for the next cycle.

Additionally or alternately cation exchange chromatography can be used.

Cation Exchange Chromatography

The total Fab solution (in ammonium acetate buffer) is applied to a cation exchange column (BioRad MacroPrep S at present though this may change to a weaker binding column in the future) where the majority of the Fab (>80%) binds. The column, and thereby the bound Fab, is then washed with three column volumes of buffer (ammonium acetate pH 4.0) to sanitize the product and remove potential contamination by prion or virus.

Once washed, the bound total Fab is eluted by washing the column with the application buffer containing sodium chloride (0.5M). The eluted Fab is then ultrafiltered and washed with saline to remove ammonium acetate buffer, concentrated as required and pumped into a sterile plastic transfer bag. This bag may be connected directly to the filling machine. The product is terminally filtered, filled and finally filled and lyophilized.

The ion exchange column is sanitized between runs using sodium hydroxide (1.0M) and then re-equilibrated with ammonium acetate buffer ready for the next cycle.

EXAMPLE 4

Biological Effect of Ovine Anti-TNFα IgG

Figure 2:
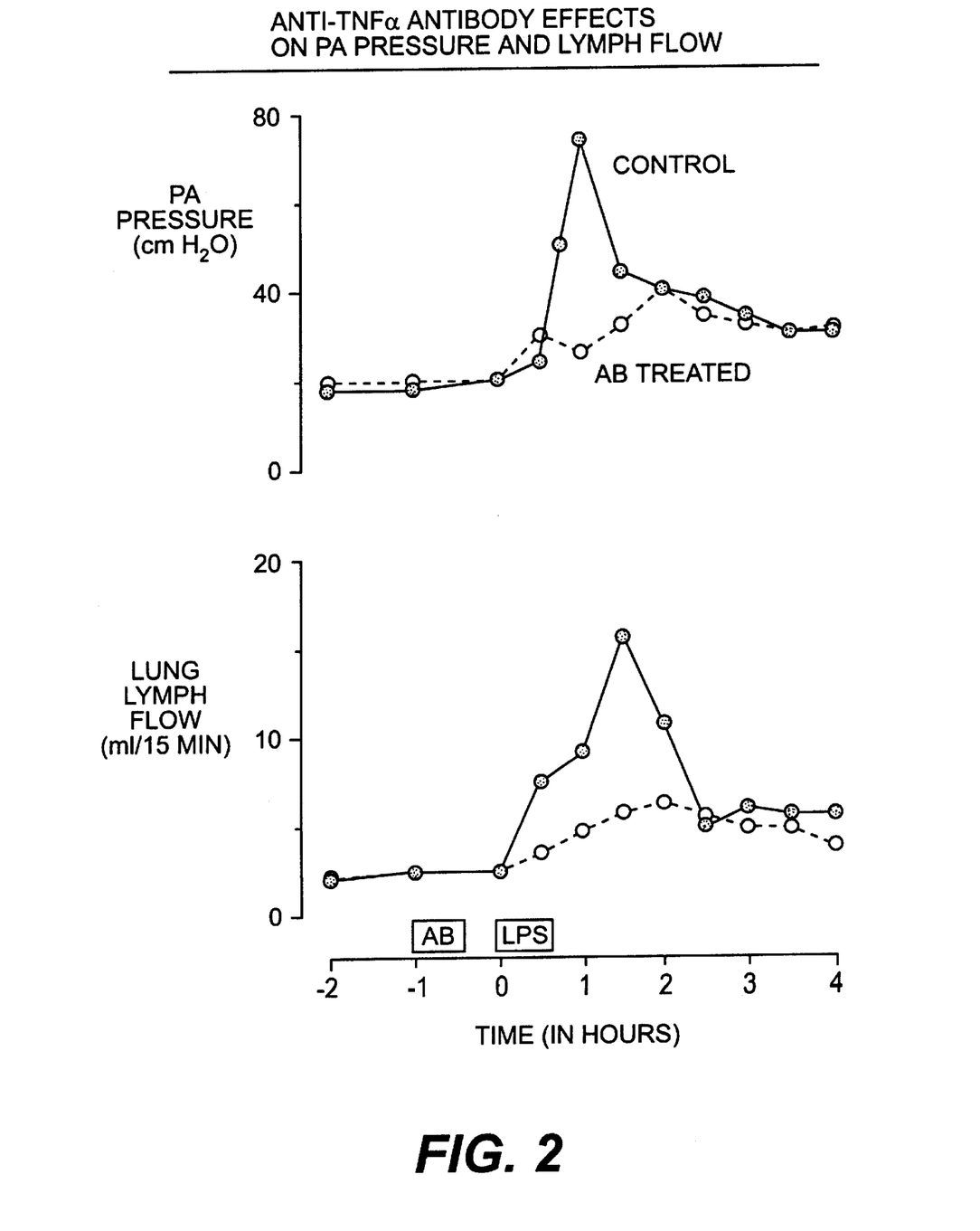
FIG. 2 shows the effect of intact anti-TNFα antibody on pulmonary artery pressure and lymph flow in the sheep.

Results of studies using intact, non-affinity purified antibodies and a sheep model for septic shock are shown in FIG. 2. The antibodies partly prevented the rise in pulmonary artery pressure and the rise in lung lymph flow which were found in the control group not given ovine anti-TNFα IgG.

EXAMPLE 5

Biological Effect of Ovine Anti-TNFα Fab Fragments in Mice

Figure 3:
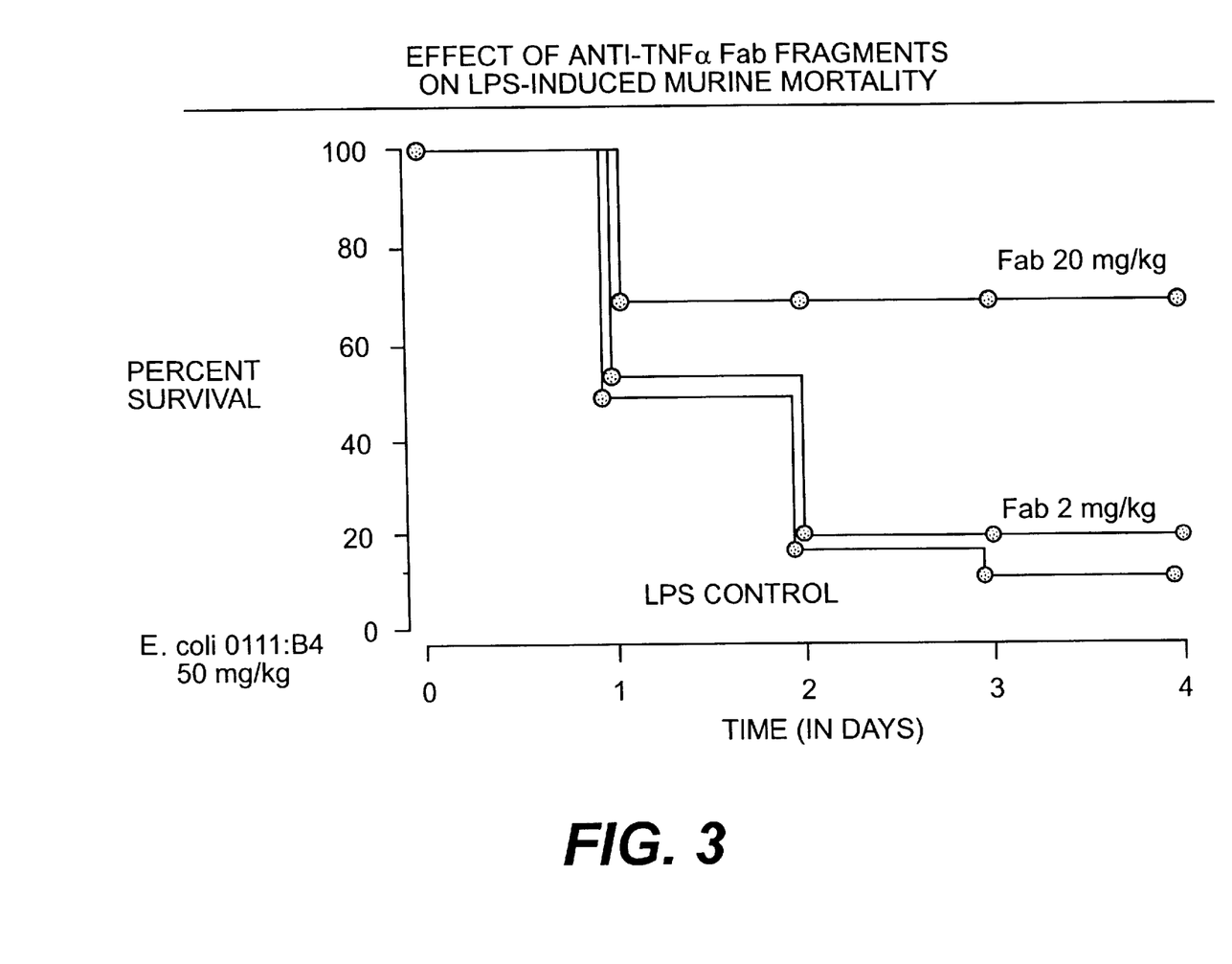
FIG. 3 shows the effect of anti-TNFα Fab fragments on lipopolysaccharide-induced mortality in the mouse.

The results of studies using specific ovine anti-TNFα Fab in mice injected with a lethal dose of endotoxin are shown in FIG. 3. Ninety percent of mice given endotoxin only were dead by day 4. This was reduced to 80% and to 30% by administration of 2 mg/kg and of 20 mg/kg of specific Fab respectively.

EXAMPLE 6

Figure 4:
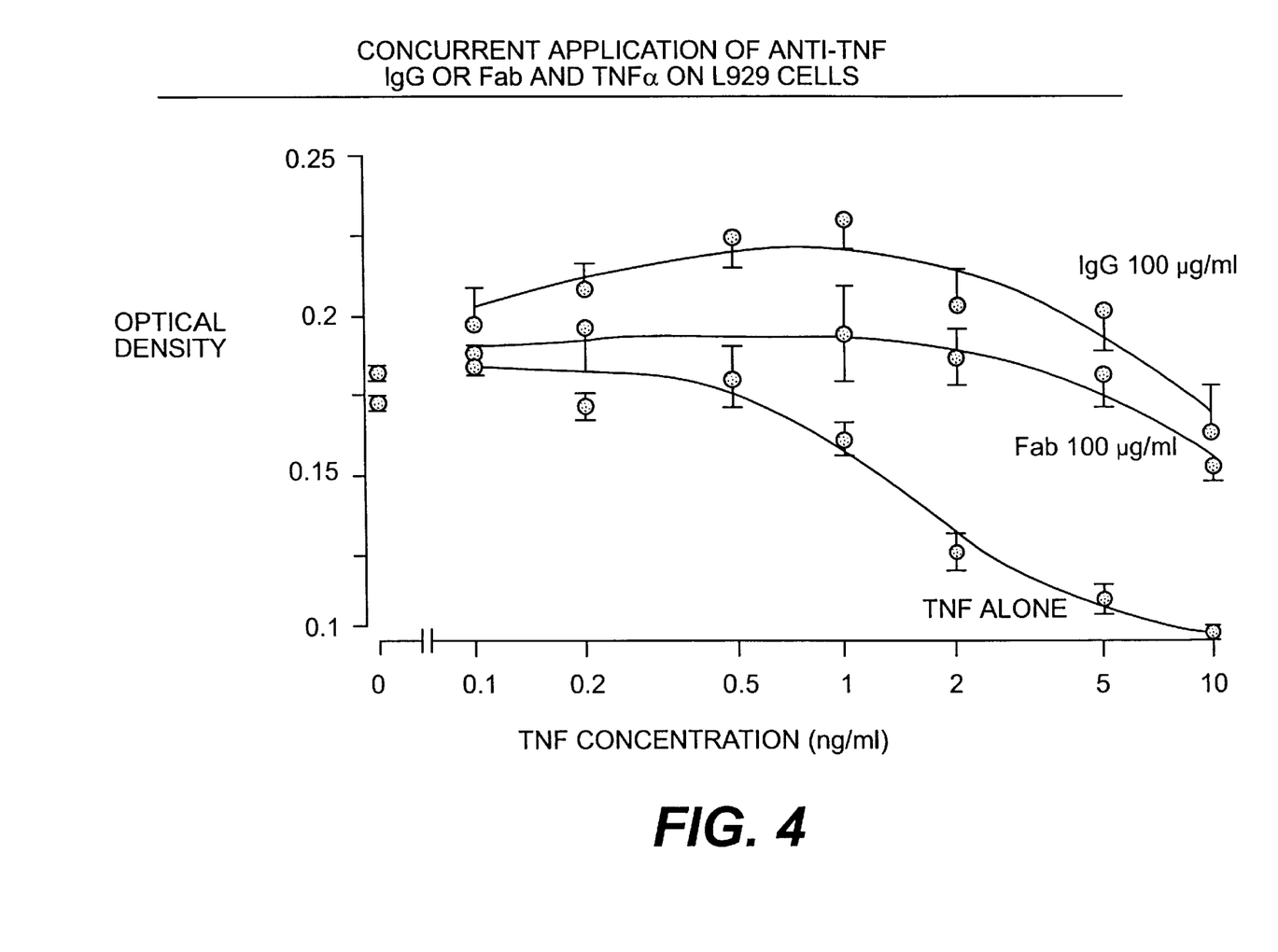
FIG. 4 shows the effect of the concurrent application of anti-TNFα IgG or Fab and TNFα on L929 cells.

Comparing the Protective Effects of Anti-TNFα IgG and Anti-TNFα Fab Fragments Against the Cytotoxic Effects of TNF We have studied the protective effects of anti-TNFα IgG and anti-TNFα Fab against the cytotoxicity of TNFα on L929 cells. When such isolated cells are cultured in vitro the addition of 10 ng/ml of TNFα to the culture medium results in their destruction (as evidenced by the fall in optical density shown in FIG. 4). Simultaneously additions of 100 μg/ml of the IgG or Fab largely protected the cells by binding to and neutralising the TNF; IgG was marginally better than Fab.

Figure 5:
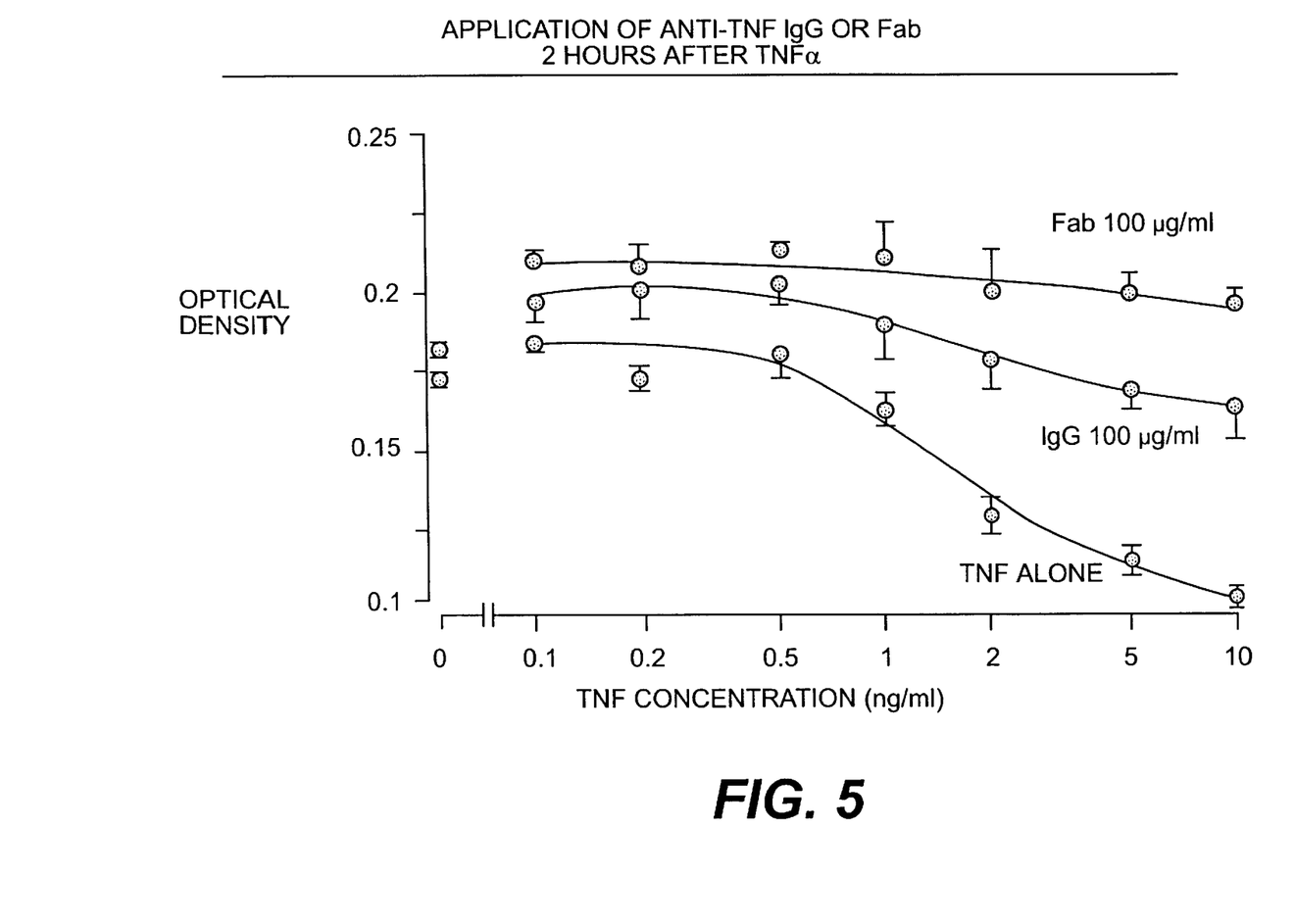
FIG. 5 shows the effect of the application of anti-TNFα IgG or Fab fragments 2 hours after TNFα treatment.
Figure 6:
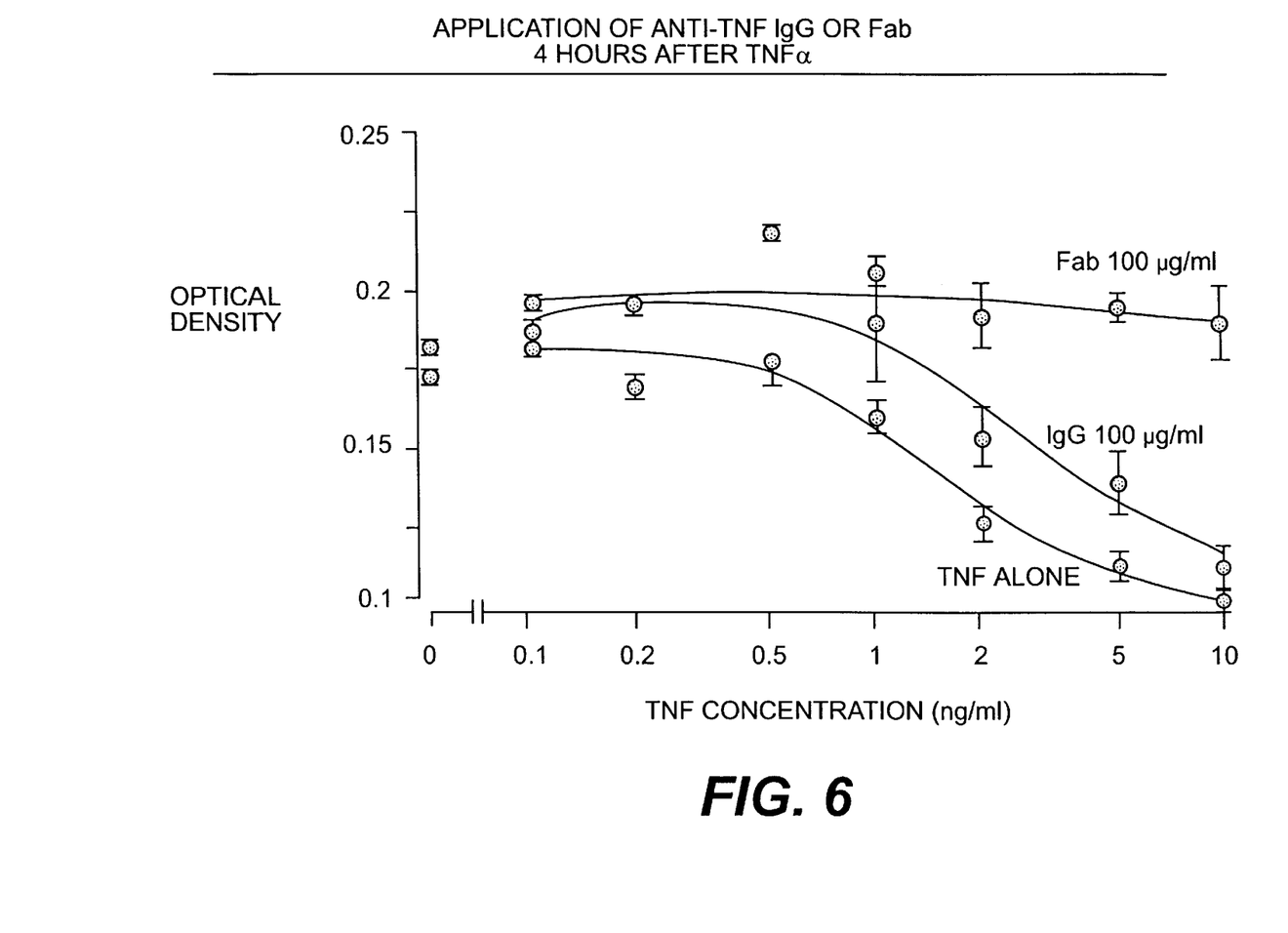
FIG. 6 shows the effect of the application of anti-TNFα IgG or Fab fragments 4 hours after TNFα treatment.

FIG. 5 and especially FIG. 6 show totally unexpected results. When addition of the antibodies is delayed for 2 or 4 hours after the addition of TNF, Fab is considerably more protective than intact IgG. Indeed, delaying the addition of the specific Fab appears to enhance the protective effects.

It is believed that these data indicate that the Fab fragments will also be useful in vivo (ie when administered to a patient) when administered with a delay of 2 or 4 hours after the increase in TNF during septic shock.

EXAMPLE 7

Clinical Trial of the Use of Anti-TNFα Fab Fragments to Prevent or Ameliorate Jarisch-Herxheimer Reaction JHR) After Antimicrobial Treatment of Louse-Borne Relapsing Fever Ethiopia remains the endemic focus for louse-borne relapsing fever (LBRF), once pandemic in Africa, the Middle East and Europe. Untreated mortality has exceeded 50% in some epidemics, but while antimicrobial treatment is effective in eliminating *Borrelia recurrentis* spirochaetaemia and preventing relapses, it is associated with a life-threatening Jarisch-Herxheimer reaction (JHR) resembling the classical endotoxin reaction. The JHR is associated with an explosive release of tumour necrosis factor (TNF), IL-6 and IL-8. A randomized double-blind controlled trial of a new ovine polyclonal Fab anti-TNF antibody was carried out in 49 patients with LBRF in Addis Ababa. For 30 minutes before they were treated with penicillin, patients were given intravenous infusions of either specific anti-TNF Fab (20 patients), control Fab (19) or isotonic saline (10). JHRs, clinically evident as rigors, were observed in 10/20 given specific Fab compared with 26/29 controls ($p<0.01$). Compared with control groups the maximum rises in temperature, pulse rate and systolic BP during the JHR were significantly less in the anti-TNF treated group ($p<0.01$, $<0.0001$, $<0.01$ respectively).

Patients presenting to the Black Lion Hospital or health clinics in the vicinity were recruited into the study if *Borrelia spirochaetes* were found in the blood film.

Exclusion Criteria

1. Children (less than 12 years old).
2. Pregnant women.
3. Elderly (more than 60 years) or severely debilitated patients with gross clinical evidence of other acute diseases, eg hypotension, marked jaundice, severe wasting and other evidence of malnutrition, severe bleeding tendency, rash of typhus, signs of active pulmonary tuberculosis or of pulmonary consolidation, state of coma, meningitis, cardiac, respiratory or coma and flapping tremor, history of recent seizures and focal neurological signs.
4. Patients with sustained violent rigors, hypotension or hyperthermia and other evidence of a spontaneous reaction ("crisis").
5. Patients taking other antibiotics.

Only patients giving informed consent to hospital admission, investigation and treatment were recruited to the study.

Baseline Information

Clinical history, including duration of and range of symptoms, and results of physical examination were recorded on a standard pro forma.

Investigations

A polytetrafluorethylene cannula was placed in the antecubital vein, fitted with a three-way tap and kept patent with heparinised saline. A baseline blood sample was drawn for microhaematocrit, total white blood cell count (WBC) spirochaete count, bilirubin, liver enzymes, creatinine or urea. A blood culture was set up to detect associated bacterial infections (especially typhoid).

A minimum of 30 patients and a maximum of 50 patients are randomised to treatment with either intravenous polyclonal anti-TNF ovine immunoglobulin Fab fragment (ATNF Fab) or an identical-looking placebo (Control Fab). 10 patients received isotonic saline only.

Early on the morning of the study, patients lay comfortably in bed. A rectal electronic thermometer probe was inserted. Blood pressure, pulse and respiratory rates were recorded.

Treatment

In patients whose baseline rectal temperatures did not fluctuate by more than 0.5° C. over a 30 minute period, 100 ml of ATNF Fab or control Fab (the contents of 4×1.5 g vials of freeze dried total Fab dissolved in 10 ml of water for injection and diluted to 100 ml with isotonic saline) or 100 ml of isotonic saline, were injected by slow intravenous infusion over 30 minutes. This dose of total immunoglobulin Fab corresponds to a dose of approximately 120 mg/kg which contains about 20 mg of specific anti-TNF Fab.

When this 30 minute infusion was completed, standard antimicrobial treatment with 600,000 units of procaine penicillin was given by intramuscular injection into the anterior thigh divided between two sites if necessary.

Assessment

Rectal temperature, blood pressure, pulse rate, respiratory rate and symptoms were recorded at the following times (0=penicillin treatment): −60, −45, −30, 0, 15, 30, 45, 60, 75, 90, 105, 120, 150, 180 min; 4, 8, and 24 hr. Venous blood will be samples for spirochaete count WBC count and cytokines (TNF$\alpha$, IL-1$\beta$, IL-8 and IL-6) at the following intervals: −30, 0, 60, 90 min; 2, 4, 8 and 24 hr.

Patients were allowed to drink throughout.

A violent JHR would be predicted 60–90 minutes after penicillin treatment.

Materials and Methods

The following procedure was used to prepare the TNF-specific ovine total Fab used in the clinical trial.

Immunogen

The TNF$\alpha$ antitoxin is an ovine Fab manufactured by immunisation of sheep with human recombinant TNF$\alpha$ (hrTNF$\alpha$). HrTNF$\alpha$ is produced in *E. coli* by expression of a synthetic gene with the sequence based on that of published cDNA for human TNF (commercially available from British Biotechnology). The recombinant protein has a molecular weight of approximately 17.5 kD and is purified to greater than 97% purity. Each lot of immunogen is tested for purity, molecular weight and cytotoxic activity before injection to the sheep. The latter is assessed using an L929 murine connective tissue cell assay.

(i) Immunisation

Groups of 10 ewes are immunised subcutaneously at six sites. Immunisation is with decreasing doses of hrTNF$\alpha$, mixed with either Freund's complete or incomplete adjuvant, following the protocol outlined in Examples 1 and 2. The sheep are immunised at monthly intervals.

(ii) Sampling and Bleeding

Two weeks after each immunisation, the sheep are either sampled (5 ml) or bled (500–700 ml) via the jugular vein. Blood is transferred to sterile, pyrogen free bottles, allowed to clot (in the case of a 5 ml sample) or gently rolled to initiate and speed clotting (in the case of bleeds). The clot is then centrifuged and the serum (as the supernatant) aspirated via sterilising (0.22 $\mu$m) filters, into gamma irradiated plastic bags.

(iii) Sample/Bleed Assessment

At six and twenty two weeks after their primary immunisation, the antibody titre of each sheep in the flock is assessed using a simple enzyme linked immunosorbent assay (ELISA).

TNF$\alpha$ is bound at high pH (9.6) to a solid-phase immunoassay plate (96 well) and increasing dilutions of the serum incubated with it. hrTNF$\alpha$-specific antibodies in the serum bind to the plate and any unbound antibody is then washed away. A second antibody, raised in donkeys to sheep immunoglobulin, is then added which has conjugated to it an enzyme (horse radish peroxidase, HRP). In the presence of a suitable substrate, HRP catalyses a chromogenic reaction, the product of which is proportional to the concentration of antibody in the sheep serum. Bleeds with a titre greater than $1/30,000$ are subsequently combined to form a 10 sheep serum pool. Sheep which fail to achieve this titre are dropped from the flock.

Individual sheep are not assessed after the twenty two week sample.

(iv) Serum Pool Assessment

Sterility and endotoxin tests are performed on each serum pool which must be sterile and contain less than 1.25 Eu/ml to be used in manufacture.

Pooling, and all subsequent manufacturing steps, are performed in clean rooms under class 100 conditions.

Pools are assessed monthly for titre, by ELISA, and for their specific antibody concentration using small scale affinity purification. This technique involves the passage of immune serum over small (1 g) hrTNF$\alpha$-Sepharose affinity columns with the selective concentration of hrTNF$\alpha$-specific IgG. These IgG may then be eluted and their concentration determined.

Pools must contain at least 2 g/l of specific antibody to be used for manufacture.

(iv) Immunoglobulin Purification

The serum immunoglobulin fraction is separated from other non-therapeutic serum proteins using salt precipitation.

Briefly, sodium sulphate (USP grade 36%, 25° C. apyrogenic and sterile) is mixed with pooled serum, over a 15 minute period, maintaining the temperature at 25° C. The precipitate from this procedure is then pelleted by centrifugation and the supernatant aspirated. The pellet is then washed twice with sterile filtered sodium sulphate solution (18%), concentrating the precipitate after each wash by centrifugation. The final pellet is resuspended in sterile isotonic (0.9%) saline and then sterile (0.2 $\mu$m) filtered.

Sterility, endotoxin purity and titre assessments are performed at this stage using:

(i) The USP sterility test (7 days growth free)
(ii) The LAL gel clot endotoxin test
(iii) Gel filtration (GF) FPLC
(iv) ELISA assay comparing with the untreated serum.

Samples of greater than 85% purity and with a titre greater than 85% that of the untreated serum are then used for Fab production. The concentration of the immunoglobulin at this stage is approximately 25 g/l as judged by optical density measurement at 280 nm (using an extinction coefficient of 15, 1% 280 nm for IgG).

(v) Enzymatic Digestion

Fab fragments of the immunoglobulin are prepared by incubation of the purified immunoglobulin with the plant enzyme papain which is itself bound to a solid-phase matrix allowing post digestion removal of the enzyme from the digest mixture.

The enzyme matrix is added to the IgG preparation in the presence of the reducing agent cysteine and EDTA (to preserve enzyme activity) and digestion allowed to progress for 24 h at 37° C. After this time the reaction is terminated by centrifugation of the mixture which removes both the immobilised enzyme from solution and the need to add large amounts of iodoacetamide blocking agent. The solution is then ultrafiltered across a 10 kD polysulphone ultrafilter (incorporating a 0.45 μm glass fibre prefilter) and washed with 10 volumes of saline (0.9%, sterile, apyrogenic) to remove all traces cysteine, EDTA and any Fc fragments. Washing procedures ensure salt contamination levels of below 2 ppm.

The sterile, apyrogenic Fab is, finally, filtered through a 0.22 μm sterilising filter. Samples are removed at this stage for quality assessment and again run on GF FPLC to monitor the efficiency of the digest and small scale affinity purification is also performed to ensure that hrTNFα-binding ability is not lost during the digestion step. Sterility and LAL tests are also performed at this stage along with spectrophotometric concentration determination. The concentration of Fab, at this stage, is approximately 60 g/l.

Sterile, apyrogenic (<10 Eu/ml) samples which show complete digestion to Fab (ie the absence of intact IgG) and which maintain at least 85% of the original serum binding capacity are deemed suitable for filling.

(vi) Filling 30 ml, neutral borosilicate glass vials are filled with 6.0 g of Fab solution and capped using butyl rubber freeze-drying stoppers. The vials are then frozen at −70° C. for a minimum of 30 minutes and then transferred to a sterile freeze dryer unit. The vials are dried for a minimum of 48 hours and then sealed under vacuum.

Vials are reconstituted in water for injection (10 ml).
The following tests are performed on the dried Fab;
(a) Full USP sterility and LAL and rabbit pyrogen endotoxin tests,
(b) Protein concentration of the reconstituted vial using μKjeldahl nitrogen analysis,
(c) Residual moisture,
(d) Purity by GF FPLC,
(e) hrTNFα neutralising ability using the L929 cell cytotoxicity assay.

QC Testing
The following tests were carried out:
In vitro
Fast Performance Liquid Chromatography (FPLC) to check purity.
Sterility.
Limulus Amoebocyte Lysate (LAL) test for pyrogen.
In vivo
Rabbit test for pyrogen.
Acute toxicity in mice and guinea pigs.
All batches were randomised for use in the double blind trial.
White Blood Cell Counts
Total WBC was counted using haemacytomer counting chambers.
Spirochaetes
Blood films were stained with Wright's stain and examined using light microscopy.
Cytokines
TNFα, IL-1β, IL-8 and IL-6 were measured by immunoassay.

Immunoradiometric assay kits for these cytokines were purchased from Medgenix Diagnostics SA, B-6220 Fleurus, Belgium.

Results

1. A severe clinical reaction was observed after the patient received saline as control. Following the fall in spirochaetes after penicillin at time zero, the respiration rises as does temperature which may reach about 107° F. The patient is particularly vulnerable in this phase and may die from the very high fever.

Figure 7:
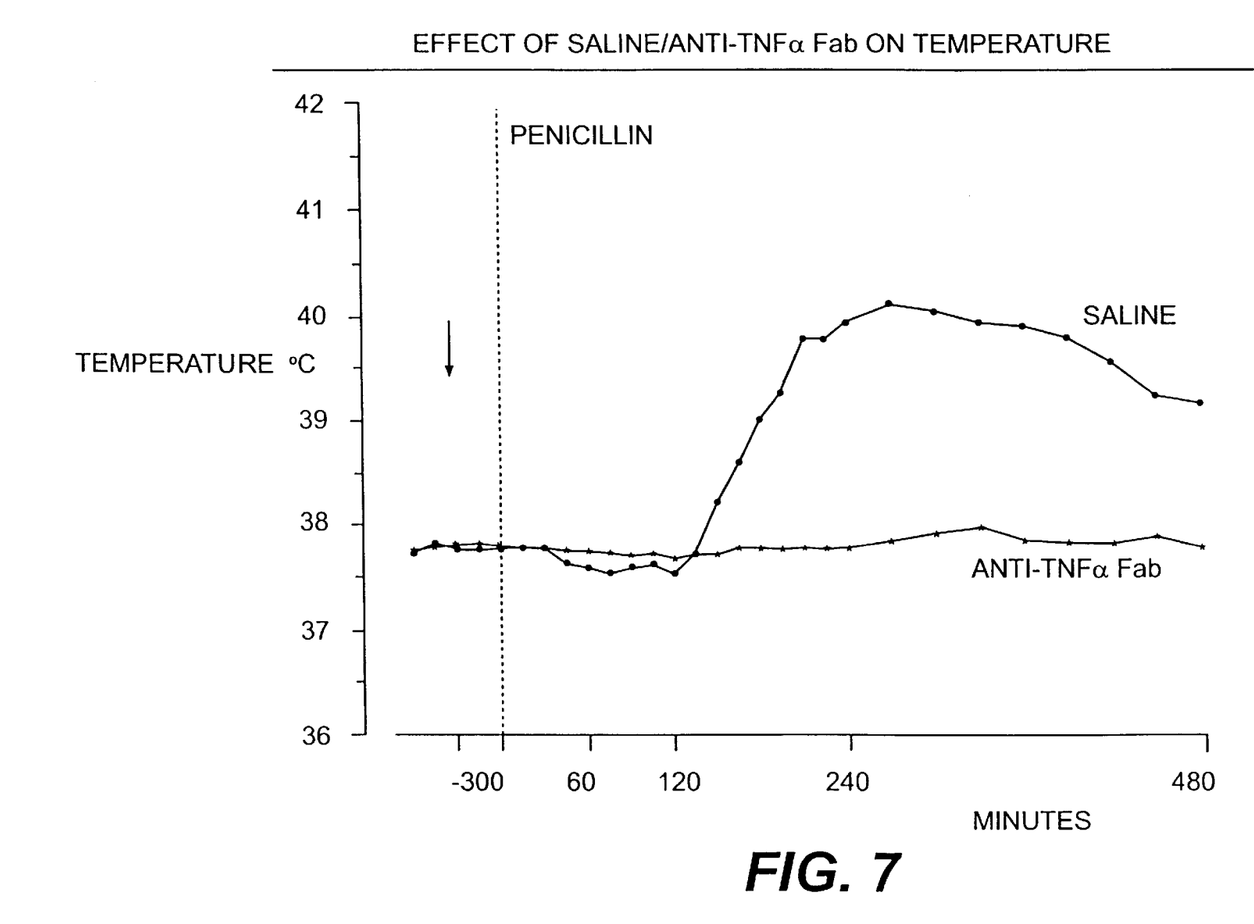
FIG. 7 shows the effect of anti-TNFα Fab fragment or saline on the temperature of the patients, when initial temperature is normal.

2. Two patients, both with normal temperature on entry into the study were treated. Note the patient receiving saline went on to develop fever whereas in the patient receiving anti-TNFα Fab the temperature remains constant (FIG. 7).

Figure 8:
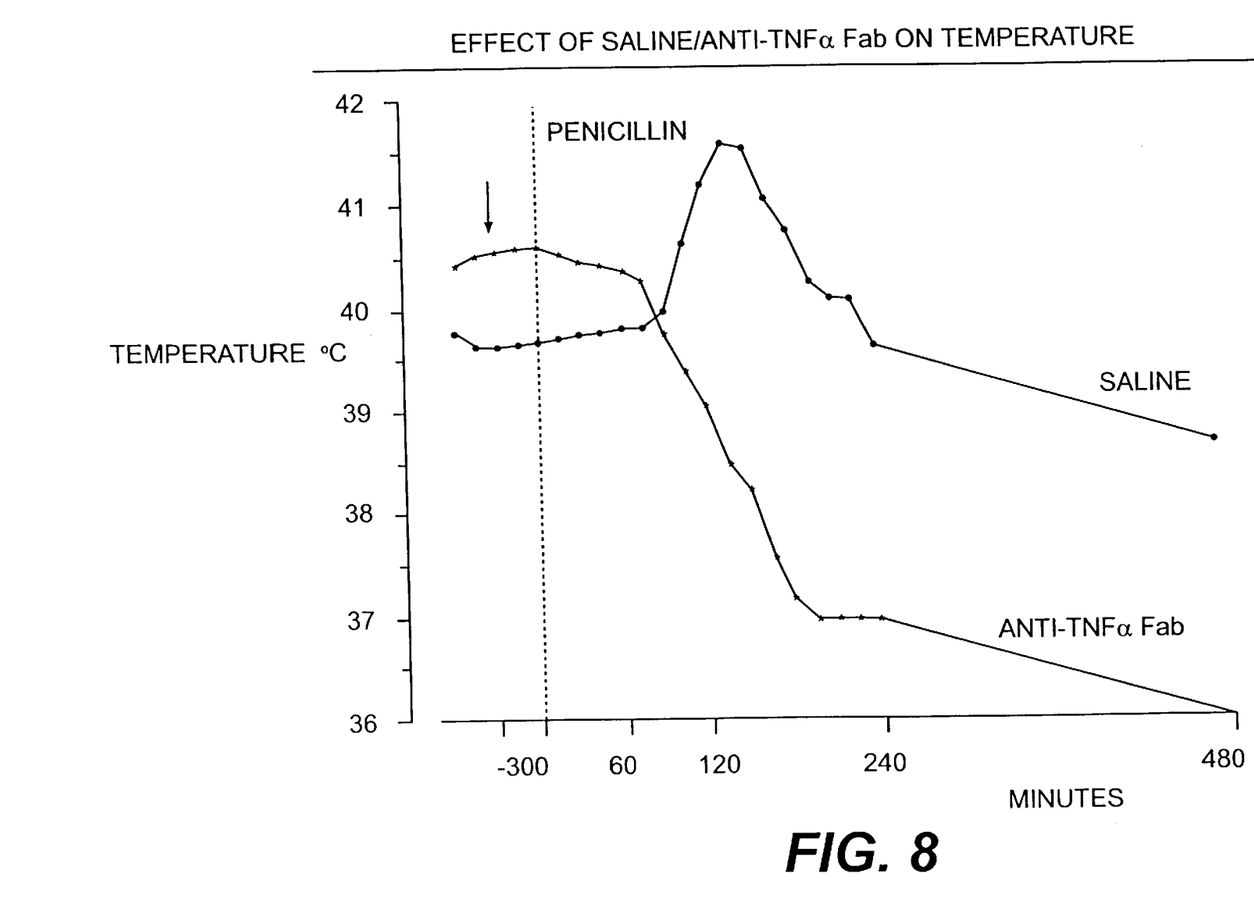
FIG. 8 shows the effect of anti-TNFα Fab fragment or saline on the temperature of the patients, when initial temperature is elevated.

3. Two patients both with high temperatures on entry into the study were treated. Note the rise in temperature in the patient receiving saline and the dramatic return to normality and prevention of the rise in temperature in the patient receiving anti-TNFα Fab (FIG. 8).

4. Study 59. Cytokine levels (IL-6, TNFα, IL-8 and IL-1B) in patients receiving saline control show no change in levels between −30 hours and 0 time (0=penicillin treatment). In most patients the levels peaked at 4 hours.

Study 027. Cytokine levels in patients receiving Fab control show no change in levels between −30 hours and 0 time (0=penicillin treatment). Levels peak at about 4 hours.

Study 004. Cytokine levels in patients receiving anti-TNFα Fab. In sharp contrast TNFα level fall dramatically between −30 hours and 0 (0=penicillin treatment). Other cytokine levels remain at admission levels or show a significantly lower peak.

Figure 9:
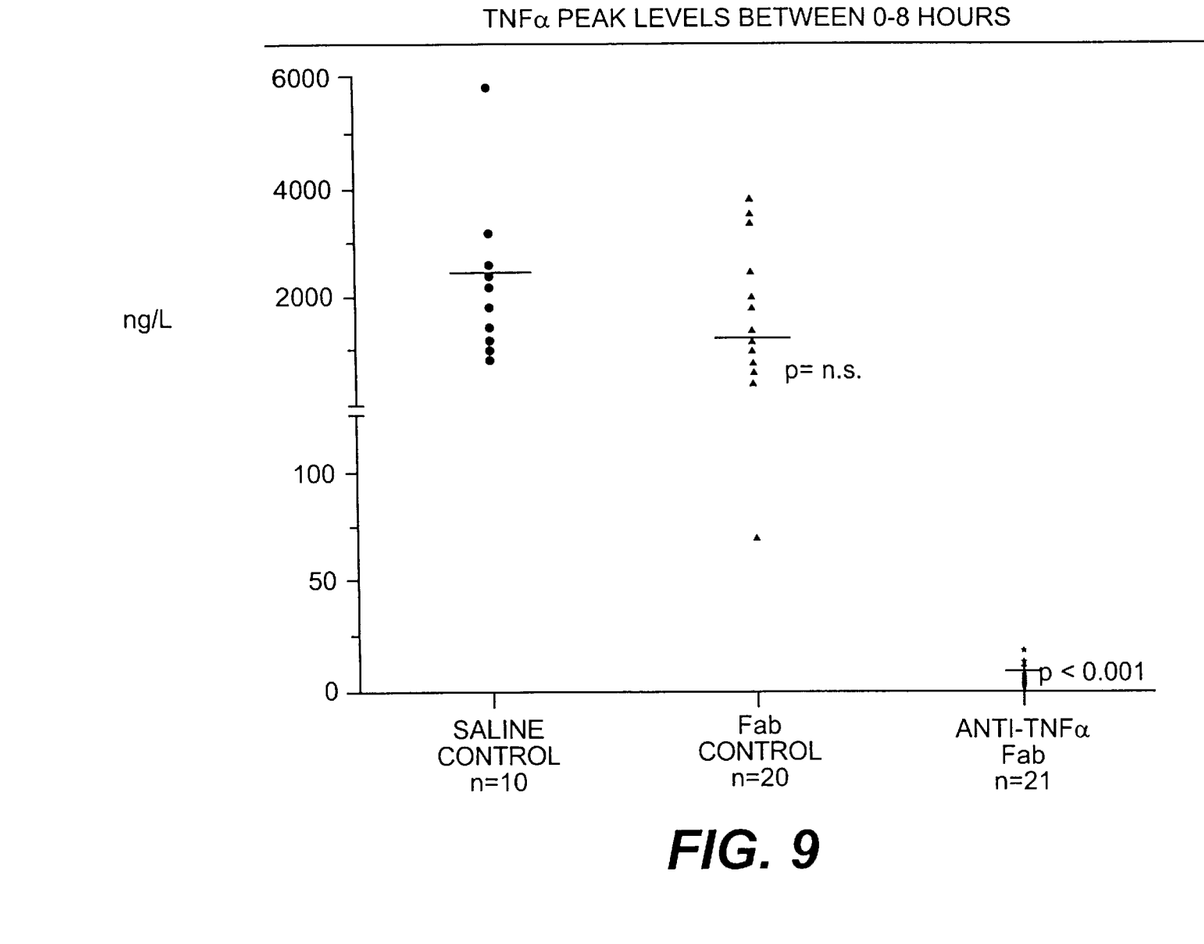
FIG. 9 shows the TNFα peak levels in patients who have been treated with saline, control Fab or anti-TNFα Fab.

FIG. 9 shows the means of TNFα peak level in patients treated with anti-TNFα Fab or control Fab compared to the saline mean. Table 2 also shows the equivalent data for IL-8 and IL-6.

TABLE 2

Cytokine peak levels between 0–8 hours

| Cytokine | Saline control mean | anti-TNF mean | p |
|---|---|---|---|
| TNF | 2200 ng/L | 10 ng/L | <0.001 |
| IL-8 | 2200 ng/L | 200 ng/L | <0.002 |
| IL-6 | 66 μg/L | 16 μg/L | <0.01 |

TABLE 3

Incidence of Jarisch-Herxheimer reaction

| Jarisch-Herxheimer reaction (J-HR) | 0 | 1+ | 2+ | 3+ | Total J-HR |
|---|---|---|---|---|---|
| Saline control | 2 | 5 | 1 | 2 | 8 |
| (%) | 20 | 50 | 10 | 20 | 80 |
| Fab control | 0 | 8 | 10 | 1 | 19 |
| (%) | 5 | 40 | 50 | 5 | 95 |
| Anti-TNFα Fab | 10 | 10 | 0 | 0 | 10 |
| (%) | 50 | 50 | 0 | 0 | 50 |

Table 3 shows the incidence of Jarisch-Herxheimer reaction in patients treated with saline control or Fab control or anti-TNFα Fab. 2+ (moderate) and 3+ (severe reactions) were not observed following treatment with anti-TNFα Fab. JHR, clinically evident as rigors, were observed in 10/20 given specific anti-TNF Fab compared with 26/29 controls (p<0.01). Compared with control groups the maximum rises in temperature, pulse rate and systolic blood pressure during JHR were significantly less in the anti-TNF treated group (p<0.01, p<0.0001 and p<0.01, respectively).

EXAMPLE 8

Treatment of Patients Receiving OKT3 Treatment With Anti-TNFα Fab Fragments

OKT3 is produced from seed lots of the parent hybridoma (ATCC CRL 8001 available from the American Type Culture Collection, 12301 Parklawn Drive, Rockville, Md. 20852-1776, U.S.A.). The immunoglobulin is purified from ascites and formulated. A treatment regime with OKT3 is described in Ortho Study Group (1985) *N. Engl. J. Med.* 313, 337–342.

The treatment regime with OKT3 is to inject 5 mg into the patient suffering from rejection of cadaveric renal transplant intravenously over the course of 2 to 4 minutes and to repeat this daily for 10 or 14 days (representing a total of 50 or 70 mg of murine monoclonal antibody). (Polyclonal anti-T-lymphocyte antisera (which are not affinity purified) may also be infused intravenously but at a much higher dose (100 to 300 mg) over a longer period (viz about 6 hours). Again such infusions are required daily for 10 to 15 days.)

During the first injection of OKT3 virtually every patient experiences severe signs and symptoms including fever in at least 90% of subjects, headaches, nausea and vomiting.

Fab fragments, prepared as described in Example 3 or 7. Endogenous TNF levels are 1 µg/l or less and are confined to the extracellular fluid compartment (about 15l). A dose of 5 mg or 10 mg of anti-TNFα Fab fragment is given at the same time as the first dose of OKT3 in order to ameliorate the effect of increased TNF levels and shock symptoms induced by OKT3 treatment. Prior to treatment with OKT3 and anti-TNFα Fab fragments the patient receives conventional immunosuppressives such as daily doses of 1.0 mg per kg of prednisone and 142 mg per kg of azathioprine. Once treatment with OKT3 and anti-TNFα Fab fragments has started the patient receives daily doses of 0.6 mg per kg of prednisone and 30 mg per kg of azathioprine.

What is claimed is:

1. A method of preventing, ameliorating, or treating septic shock or the symptoms of septic shock in a human patient, comprising administering to the human patient IgG Fab fragments reactive towards TNFα, wherein the IgG Fab fragments are derived from polyclonal IgG.

2. A method of preventing the Jarisch-Herxheimer reaction in a human patient, comprising administering to the human patient polyclonal IgG Fab fragments, wherein said Fab fragments bind to TNFα, and wherein said Fab fragments are administered to the human patient before an antimicrobial agent is administered to the human patient.

3. A method according to claim 1 wherein the human patient is suffering from septic shock or the symptoms of septic shock.

4. A method according to claim 3, wherein the symptoms of septic shock are caused by the administration of the monoclonal antibody OKT3 or a functionally equivalent antibody.

5. A method according to claim 3, wherein the symptoms of septic shock are caused by the Jarisch-Herxheimer reaction.

6. The method of claim 1, wherein said Fab fragments are administered before the human patient has developed elevated levels of TNFα.

7. The method of claim 1, wherein said Fab fragments are administered after the human patient has developed elevated levels of TNFα.

8. The method of claim 7, wherein said Fab fragments are administered two hours after the human patient has developed elevated levels of TNFα.

9. The method of claim 7, wherein said Fab fragments are administered four hours after the human patient has developed elevated levels of TNFα.

10. The method of claim 1 or 2, wherein said IgG Fab fragments prevent a rise in the pulmonary artery pressure in the human patient.

11. The method of claim 1 or 2, wherein said IgG Fab fragments prevent a rise in the lung lymph flow in the human patient.

12. The method of claim 1 or 2, wherein said IgG Fab fragments prevent a rise in the pulse rate in the human patient.

13. The method of claim 1 or 2, wherein said IgG Fab fragments prevent a rise in the temperature of the human patient.

14. The method of claim 1 or 2, wherein said IgG Fab fragments prevent a rise in the systolic blood pressure in the human patient.

* * * * *